United States Patent
Beane et al.

(10) Patent No.: US 8,679,138 B2
(45) Date of Patent: *Mar. 25, 2014

(54) APPARATUS AND METHOD FOR FORMING A HOLE IN A HOLLOW ORGAN

(75) Inventors: Richard M. Beane, Hingham, MA (US); John W. Brown, Indianapolis, IN (US); James Alan Crunkleton, Weston, MA (US); James S. Gammie, Stevenson, MD (US); Joseph L. Smith, Jr., Concord, MD (US)

(73) Assignee: Correx, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/924,138

(22) Filed: Sep. 21, 2010

(65) Prior Publication Data

US 2011/0196408 A1 Aug. 11, 2011

Related U.S. Application Data

(63) Continuation of application No. 11/581,081, filed on Oct. 16, 2006, now Pat. No. 7,799,041, which is a continuation-in-part of application No. 11/086,577, filed on Mar. 23, 2005, now Pat. No. 7,510,561.

(60) Provisional application No. 60/555,308, filed on Mar. 23, 2004, provisional application No. 60/635,652, filed on Dec. 14, 2004, provisional application No. 60/636,449, filed on Dec. 15, 2004, provisional application No. 60/726,222, filed on Oct. 14, 2005.

(51) Int. Cl.
*A61B 17/11* (2006.01)

(52) U.S. Cl.
USPC .......................................... 606/153; 606/184

(58) Field of Classification Search
USPC ................... 606/141, 153, 184, 185
See application file for complete search history.

(56) References Cited

U.S. PATENT DOCUMENTS

| 4,118,806 A | 10/1978 | Porier et al. |
| 4,769,031 A | 9/1988 | McGough et al. |

(Continued)

FOREIGN PATENT DOCUMENTS

| WO | WO 82/01644 | 5/1982 |
| WO | WO 93/00868 | 1/1993 |

(Continued)

OTHER PUBLICATIONS

Brown et al., Apicoaortic Valved Conduits for Complex Left Ventricular Outflow Obstruction: Technical Considerations and Current Status, The Annals of Thoracic Surgery, Aug. 1984, pp. 162-168, vol. 38, No. 2, Little, Brown and Company, Boston, Massachusetts.

(Continued)

*Primary Examiner* — Ryan Severson
(74) *Attorney, Agent, or Firm* — Pandiscio & Pandiscio

(57) ABSTRACT

The invention relates to an apparatus and method for forming a hole in a wall of a hollow organ. The applicator includes a hole forming element for forming a hole in the wall of the organ, a positioning means for positioning the hole forming element, and a retractor element. In addition, the applicator includes a sequencing means for coordinating the relative movement of the retractor element and the hole forming element in a sequential manner to thereby carry out a procedure for forming a hole in the wall of the hollow organ. The sequencing means may further include a safety latch element operatively coupled to the retracting means and the hole forming element. The safety latch of the invention keeps prevents damage to the internal surface of the organ during the formation of the hole.

11 Claims, 13 Drawing Sheets

(56) References Cited

U.S. PATENT DOCUMENTS

| | | | |
|---|---|---|---|
| 4,794,928 | A | 1/1989 | Kletschka |
| 5,129,913 | A | 7/1992 | Ruppert |
| 5,192,290 | A | 3/1993 | Hilal |
| 5,500,014 | A | 3/1996 | Quijano et al. |
| 5,843,088 | A | 12/1998 | Barra et al. |
| 6,083,237 | A | 7/2000 | Huitema et al. |
| 6,098,629 | A | 8/2000 | Johnson et al. |
| 6,146,325 | A | 11/2000 | Lewis et al. |
| 6,266,550 | B1 | 7/2001 | Selmon et al. |
| 6,409,739 | B1 | 6/2002 | Nobles et al. |
| 6,416,527 | B1 | 7/2002 | Berg et al. |
| 6,471,713 | B1 | 10/2002 | Vargas et al. |
| 6,475,222 | B1 | 11/2002 | Berg et al. |
| 6,551,350 | B1 | 4/2003 | Thornton et al. |
| 6,712,831 | B1 | 3/2004 | Kaplan et al. |
| 6,726,648 | B2 | 4/2004 | Kaplon et al. |
| 6,827,735 | B2 | 12/2004 | Greenberg |
| 6,843,803 | B2 | 1/2005 | Ryan et al. |
| 6,863,677 | B2 | 3/2005 | Breznock |
| 6,893,460 | B2 | 5/2005 | Spenser et al. |
| 6,942,672 | B2 | 9/2005 | Heilman et al. |
| 6,994,666 | B2 | 2/2006 | Shannon et al. |
| 7,077,801 | B2 | 7/2006 | Haverich |
| 2001/0004675 | A1 | 6/2001 | Woodard et al. |
| 2001/0004697 | A1 | 6/2001 | Blatter et al. |
| 2001/0005787 | A1 | 6/2001 | Oz et al. |
| 2001/0025643 | A1 | 10/2001 | Foley |
| 2002/0045846 | A1 | 4/2002 | Kaplon et al. |
| 2002/0082467 | A1 | 6/2002 | Campbell |
| 2002/0082614 | A1 | 6/2002 | Logan et al. |
| 2002/0108621 | A1 | 8/2002 | Berg et al. |
| 2002/0173808 | A1 | 11/2002 | Houser et al. |
| 2002/0183584 | A1 | 12/2002 | Shannon et al. |
| 2002/0183769 | A1 | 12/2002 | Swanson et al. |
| 2003/0023255 | A1 | 1/2003 | Miles et al. |
| 2003/0040765 | A1 | 2/2003 | Breznock |
| 2003/0078592 | A1 | 4/2003 | Heilman et al. |
| 2003/0100816 | A1 | 5/2003 | Siess |
| 2003/0130668 | A1 | 7/2003 | Nieman et al. |
| 2003/0204198 | A1 | 10/2003 | Berg et al. |
| 2004/0002624 | A1 | 1/2004 | Yu et al. |
| 2004/0002719 | A1 | 1/2004 | Oz et al. |
| 2004/0059178 | A1 | 3/2004 | McCarthy et al. |
| 2004/0116769 | A1 | 6/2004 | Jassawalla et al. |
| 2004/0162608 | A1 | 8/2004 | Haverich |
| 2004/0171905 | A1 | 9/2004 | Yu et al. |
| 2004/0193004 | A1 | 9/2004 | Tsubouchi et al. |
| 2005/0033107 | A1 | 2/2005 | Tsubouchi |
| 2005/0149093 | A1 | 7/2005 | Pokorney |
| 2006/0036313 | A1 | 2/2006 | Vassiliades |
| 2006/0089707 | A1 | 4/2006 | Vassiliades et al. |
| 2006/0161193 | A1 | 7/2006 | Beane et al. |
| 2006/0241544 | A1 | 10/2006 | Haverich |
| 2007/0055357 | A1 | 3/2007 | Pokorney et al. |

FOREIGN PATENT DOCUMENTS

| | | |
|---|---|---|
| WO | WO 97/27897 | 8/1997 |
| WO | WO 2004/073555 | 9/2004 |
| WO | WO 2005/094525 | 10/2005 |

OTHER PUBLICATIONS

Carrel, On the Experimental Surgery of the Thoracic Aorta and the Heart, May 5, 1910, pp. 83-95.

Sarnoff et al., The Surgical Relief of Aortic Stenosis by Means of Apical-Aortic Valvular Anastomosis, Circulation, Journal of the American Heart Association, Apr. 1955, pp. 564-575.

APPARATUS AND METHOD FOR FORMING A HOLE IN A HOLLOW ORGAN

RELATED APPLICATION DATA

This patent application is a continuation of prior U.S. patent application Ser. No. 11/581,081, filed Oct. 16, 2006, now U.S. Pat. No. 7,799,041, by Richard M. Beane et al. for APPARATUS AND METHOD FOR FORMING A HOLE IN A HOLLOW ORGAN, which in turn is (1) a continuation-in-part of prior U.S. patent application Ser. No. 11/086,577, filed Mar. 23, 2005, now U.S. Pat. No. 7,510,561, by Richard M. Beane et al. for APPARATUS AND METHOD FOR CONNECTING A CONDUIT TO A HOLLOW ORGAN, which in turn claims benefit of (i) prior U.S. Provisional Patent Application Ser. No. 60/555,308, filed Mar. 23, 2004 by Joseph L. Smith, Jr. et al. for APPARATUS AND METHOD FOR CONNECTING A CONDUIT TO A HOLLOW ORGAN; (ii) prior U.S. Provisional Patent Application Ser. No. 60/635,652, filed Dec. 14, 2004 by James Alan Crunkleton et al. for APPARATUS AND METHOD FOR CONNECTING A CONDUIT TO A HOLLOW ORGAN; and (iii) Prior U.S. Provisional Patent Application Ser. No. 60/636,449, filed Dec. 15, 2004 by James Alan Crunkleton et al. for APPARATUS AND METHOD FOR CONNECTING A CONDUIT TO A HOLLOW VESSEL; and (2) claims benefit of prior U.S. Provisional Patent Application Ser. No. 60/726,222, filed Oct. 14, 2005 by Richard M. Beane et al. for APPARATUS AND METHOD FOR CONNECTING A CONDUIT TO A HOLLOW ORGAN.

FIELD OF THE INVENTION

The present invention relates to an apparatus and method for forming a hole in a hollow organ, and more particularly, to a surgical device and method for forming a hole in a heart.

BACKGROUND OF THE INVENTION

As the average age of the United States population increases, so do the instances of aortic stenosis. An alternative approach to the conventional surgical replacement of the stenotic aortic valve involves the use of an apicoaortic conduit. In this approach, the native aortic valve is not removed, and a prosthetic valve is implanted in a parallel flow arrangement. A connection conduit (or tube) connects the apex of the heart to the descending aorta. Somewhere along this conduit, the prosthetic valve is interposed. Thus, blood leaves the heart through the apex and travels through the conduit (with valve) to the descending aorta.

Until recently, surgical procedures to implant an apicoaortic conduit have included a single, long incision, such as in the 6th intercostal space, to expose the heart and allow retraction of the lungs to expose the descending aorta. Recognizing the potential for broader scale use of the apicoaortic conduit for aortic valve replacement, some surgeons are now attempting to use smaller incisions and are requesting development of surgical tools for a minimally invasive procedure. As an initial attempt to make the procedure less invasive, some surgeons have recently performed the following procedure.

The patient is placed on the table in the supine, position. Anesthesia is induced, and the patient is intubated with a double-lumen endotracheal tube, this facilitates one-lung ventilation and allows the surgeon to work within the left chest. The patient is positioned with the left side up (90 degrees). The pelvis is rotated about 45 degrees, such that the femoral vessels are accessible. An incision is made over the femoral vessels, and the common femoral artery and vein are dissected out. Heparin is administered. Pursestring sutures are placed in the femoral artery and vein. The artery is cannulated first, needle is inserted into the artery, and a guidewire is then inserted. Transesophageal echo is used to ascertain that the wire is in the descending aorta. Once this is confirmed, an arterial cannula is inserted over the wire. into the artery (Seldinger technique). The arterial cannula is typically 19 or 21 French. Once inserted, the pursestring sutures are snugged down over tourniquets. A similar procedure is followed for the femoral vein. The venous cannula is usually a few French larger than the arterial cannula. Once both vein and artery are cannulated, the cannulae are connected to the cardiopulmonary bypass, and the capability to initiate cardiopulmonary bypass at any time is present.

A 1 cm incision is made in approximately the 7th interspace in the posterior axillary line; the videoscope (10 mm diameter) is inserted, and the left chest contents viewed. The location of the apex of the heart is determined, and the light from the scope used to transilluminate the chest wall, which allows precise localization of the incision. The incision is then performed. It is essentially an anterior thoracotomy, typically in the 6th interspace. Recent incisions have been about 10 cm long, but are expected to become smaller and smaller with time. A retractor is inserted and the wound opened gently. A lung retractor is used to move the (deflated) left lung cephalad. The descending aorta is dissected free from surrounding soft tissue to prepare for the distal anastomosis. This dissection includes division of the inferior pulmonary ligament. A pledgeted suture is placed on the dome of the diaphragm and positioned to pull the diaphragm toward the feet (out of the way). The pericardium is incised about the apex of the heart, and the apex is freed up and clearly identified.

On the back table, the apicoaortic conduit is prepared, such as a 21 Freestyle valve sutured on the inflow opening to an 18-mm Medtronic apical connector and sutured on the outflow opening to a 20-mm Hemashield graft. The Dacron associated with the apical connector is pre-clotted with thrombin and cryoprecipitate. The assembly is brought to the field, and a measurement made from the apex of the heart to the descending aorta. The assembly is trimmed appropriately. A partial-occluding clamp is then placed on the descending aorta, and the aorta opened with a knife and scissors. The conduit (the end with the 20 mm Hemashield graft) is then sutured to the descending aorta using 4-0 prolene suture, in a running fashion. Once this is complete, the clamp is removed and the anastomosis checked for hemostasis. Blood is contained by the presence of the Freestyle aortic valve. The apical connector is placed on the apex, and a marker is used to trace the circular outline of the connector on the apex, in the planned location of insertion. Four large pledgeted sutures (mattress sutures) of 2-0 prolene are placed; one in each quadrant surrounding the marked circle. The sutures are then brought through the sewing ring of the apical connector. A stab wound is made in the apex in the center of the circle, and a tonsil clamp is used to poke a hole into the ventricle. Bypass may be initiated at this point, but some surgeons have developed crude manual techniques to avoid bypass entirely. A Foley catheter is inserted into the ventricle, and the balloon expanded. A cork borer is then used to cut out a plug from the apex. The connector is then parachuted down into position. A rotary motion is necessary to get the connector to seat in the hole. The four quadrant sutures are tied, and hemostasis is checked. If there is a concern regarding hemostasis, additional sutures are placed. The retractor is removed, chest tubes are placed, and the wound is closed.

Surgical tools developed specifically to implant the apicoaortic conduit are expected to provide the means for a much less invasive procedure. The procedure is expected to be performed with a series of smaller thoracotomy incisions between the ribs, such as immediately over the apex of the heart. In addition to avoiding the median sternotomy, development of appropriate surgical tools is expected to avoid the need for cardiopulmonary bypass, so that the procedure can be performed on a beating heart. The diseased aortic valve does not need to be exposed or excised. The stenotic aortic valve is left in place and continues to function at whatever level it remains capable of, and the apicoaortic conduit accommodates the balance of aortic output.

The major obstacle to widespread adoption of this superior configuration is the nearly complete lack of efficient devices to perform the procedure. Surgeons wishing to adopt the procedure must gather a collection of instruments from a variety of manufacturers. Often these instruments were created for quite different purposes, and the surgeon is forced to adapt them as required and manually manipulate them during a procedure.

U.S. Published Patent Application 2005/0149093 A1 (Pokorney) describes a device for implanting an apicoaortic conduit between the apex of the heart and the descending aorta. The device for cannulating the apex uses a piercing and dilating approach to avoid cutting a tissue plug. Substantial force may be required to cut and dilate a hole to place the conduit to its final position. The force may significantly deform the heart to prevent placement of the conduit or even harm internal heart structures.

U.S. Published. Patent Application 2003/0130668 A1 (Nieman) describes ideas for remotely cannulating a body part, such as a heart. The method and apparatus are endoscopic, i.e. the instruments are mounted on the end of a long flexible member and inserted into the body through a trocar, i.e., a sharply pointed surgical instrument contained in a cannula. The endoscopic procedure appears complicated. After the device is placed at or near the apex of the heart, the surgeon or some other controller performs at least 13 separate steps to secure the cannula in the heart wall. Coordination of these steps with a user-friendly interface may be challenging. An attachment ring (which includes an apical ring and a locking stem) is sutured to the heart wall, and subsequently the cannula is connected to the attachment ring as a separate step. Because the procedure is endoscopic, imaging means (e.g., fluoroscopy) is used to place a balloon at the correct depth within the ventricle to provide occlusion.

The complex endoscopic procedure disclosed in Nieman appears to require that the cut tissue core be removed from the body prior to advancing the cannula to the heart wall. Further, Nieman appears to provide two mechanisms for placing the cannula in the heart wall. One such mechanism is to create a hole that is large enough to easily slide the cannula into the hole. This does not provide a tight fit between the cannula and cored heart wall to prevent blood loss from the cored heart wall and from the ventricle and relies entirely upon the sutured attachment ring to achieve hemostasis thus providing a period of time during which there could be great losses of blood. The second mechanism is to achieve a tight (interference) fit between the cannula and cored hole. However, such a tight fit requires substantial axial and torsional forces to be applied to the cannula. The flexible endoscopic instrument disclosed in Nieman may not provide such forces to be transmitted.

U.S. Pat. No. 7,077,801 (Haverich) discloses various approaches for implanting a conduit into the wall of a heart. As illustrated in FIG. 8A, Haverich shows a conduit on a cutter that has a "corkscrew driver" with a coil. The corkscrew is rotated to cause the cutter to penetrate through the myocardium. However, substantial axial force is required to cleanly penetrate the myocardium, and such force is not easily applied by a corkscrew. Further, the pointed tip of the corkscrew can damage other areas of the heart wall (e.g., the septum) while applying axial force and rotation. Haverich discloses a balloon used for hemostasis. However, the balloon is a separate instrument that cannot be combined with the corkscrew.

U.S. Pat. No. 6,726,648 (Kaplon) discloses a device similar to Haverich except that a trocar is used to penetrate the organ wall instead of a cutter with corkscrew. No tissue plug is formed with a trocar, but substantial force may be required. Use of a trocar makes it difficult to achieve hemostasis during a procedure on a beating heart. To address this, rigid conduit 18 is inserted through the connector 16 after the connector is implanted with the trocar and sewn into place. Connector 16 does not appear to penetrate the heart wall. Connector 16 has a built-in valve to prevent blood loss after the trocar is removed and until conduit 18 is inserted.

U.S. Pat. No. 6,942,672 (Heilman) discloses another device for implanting a conduit to the heart wall that uses a sealed enclosure to eliminate air and to prevent blood loss.

SUMMARY OF THE INVENTION

The invention relates to an applicator for forming a hole in a wall of a hollow organ. The applicator includes a hole forming element for forming a hole in the wall of the organ, the hole forming element having a cutting element on a distal end thereof. The applicator also includes a positioning means coupled to the hole forming element for positioning the hole forming element, a retractor element operatively coupled to the positioning means, and a sequencing means for coordinating the relative movement of the retractor element and the hole forming element in a sequential manner to thereby carry out a procedure for forming a hole in the wall of the hollow organ.

The invention also relates to a method of forming a hole in a wall of a hollow organ. The method includes steps of forming a hole in the wall of the organ with a hole forming element, the hole forming element having a cutting element on a distal end thereof, positioning the hole forming element with a positioning means coupled to the hole forming element, the positioning means being operatively coupled to a retractor element, and coordinating the relative movement of the retractor element with respect to the hole forming element in a sequential manner with a sequencing means to thereby carry out a procedure for forming a hole in the wall of the hollow organ.

The retractor element may comprise a retractor body movably disposed within the hole forming element and an expansion element disposed on a distal end of the retractor body, and the expansion element may be expandable from an unexpanded state to fully expanded state and to a partially expanded state. The sequencing means may control the expansion of the expansion element from the unexpanded state, to the fully expanded state, and to the partially expanded state in a sequential manner. In addition, the sequencing means may include a safety latch element operatively coupled to the retracting means and the hole forming element, and may further include a sequencing bolt that extends through a cylinder cam slot formed in the retractor element, a pusher cam slot formed in a pusher element, and a safety latch cam slot formed in the safety latch element.

In this case, the sequencing means comprises a means for causing the elements to assume the following states in seriatim:

a) a first state in which the sequencing bolt moves from a first position to a second position in each of the cylinder cam slot, the pusher cam slot, and the safety latch cam slot, thereby expanding the expansion element to a fully expanded state while retaining the retractor element in a fully extended position relative to the hole forming element;

b) a second state in which the sequencing bolt moves from the second position to a third position in the cylinder cam slot, the pusher cam slot, and the safety latch cam slot, thereby retaining the expansion element in the fully expanded state and the retractor element in the fully extended position;

c) a third state in which the sequencing bolt moves from the third position to a fourth position in the cylinder cam slot, the pusher cam slot, and the safety latch cam slot, thereby permitting the retractor element to move towards the hole forming element while retaining the expansion element in the fully expanded state;

d) a fourth state in which the sequencing bolt is locked in a fourth position in the safety latch cam slot, the cylinder cam slot, and the pusher cam slot, thereby retaining the expansion element in the fully expanded state;

e) a fifth state in which the safety latch element is moved relative to the retractor element such that the sequencing bolt is repositioned from the fourth position to a fifth position in the safety latch cam slot while remaining in the fourth position in the cylinder cam slot and the pusher cam slot, thereby releasing the expansion element in the fully expanded state; and f) a sixth state in which the sequencing bolt moves from the fifth position to a sixth position in the safety latch cam slot, and simultaneously, from the fourth position to a fifth position in the cylinder cam slot and the pusher cam slot, to allow the expansion element to assume the partially expanded state.

Accordingly, the invention provides a safety latch that keeps the expansion element in a fully expanded state (i.e. the fourth state) covering the sharp edge of the cutting element to protect the inner surfaces of the hollow organ (i.e. the heart) until the safety latch is released by a deliberate action of the surgeon. In this way, the surgeon can push and rotate the hole forming element while positioning the connector conduit in the apex wall without damaging the inner surfaces of the heart.

In addition, the invention provides a safety latch that the surgeon cannot deliberately or inadvertently release before the sequencing bolt is at the proper position. Furthermore, the invention provides relief to the requirement that the expansion element be moved to be at least partially disposed in the hole forming element, thereby preventing sticking of the cam mechanism during reloading. Also, the invention provides an applicator that cuts a hole in the heart wall without simultaneously implanting a connector conduit in the heart wall.

DETAILED DESCRIPTION OF THE INVENTION

Figure 1:
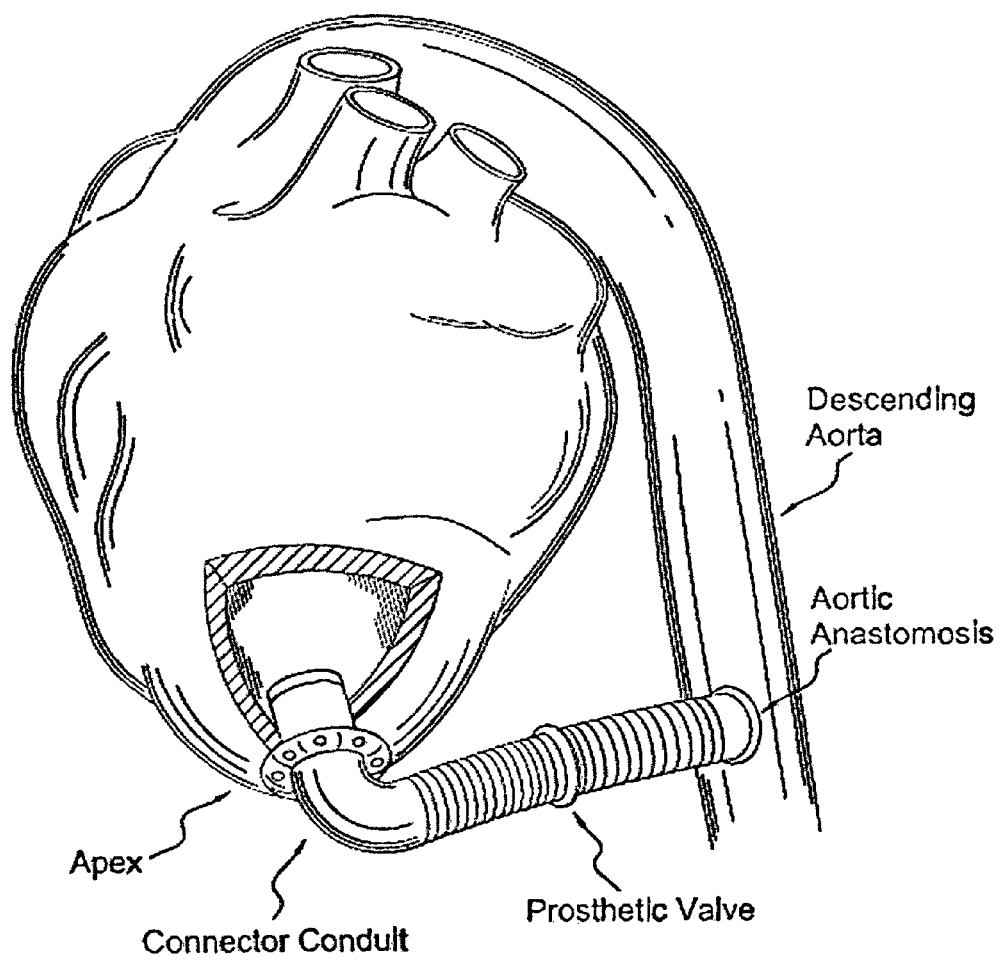
FIG. 1 illustrates an exemplary apicoaortic conduit.

Referring now to the figures, related U.S. Patent Application Publication No. 2005-0251187 to Beane, et al., which is incorporated herein by reference in its entirety, describes use of a sequencing element (such as a cam mechanism) that helps to ensure that critical steps of implanting a connector conduit into the apex of the left ventricle are performed in the proper sequence. (See FIG. 1). Once a tissue plug is created, the sequencing element partially reduces the diameter of the expanding element so that the expanding element can enter the inner diameter of the cutting element while remaining of large enough diameter to prevent the tissue plug from sliding off of the retractor element.

For example, the '187 patent application publication relates to an applicator for forming a hole in a wall of a hollow organ and for inserting a connector conduit into the hole to facilitate connection of the connector conduit to the hollow organ. The applicator includes a hole forming element for forming a hole in the wall of the organ, a positioning means coupled to the hole forming element for positioning the hole forming element, a retractor element operatively coupled to the positioning means, and a sequencing means for coordinating the relative movement of the retractor element with respect to the hole forming element in a sequential manner to thereby carry out a procedure for forming a hole in the wall of the hollow organ and inserting the connector conduit in the hole.

The hole forming element has a cutting element on a distal end thereof and is adapted for coupling with the connector conduit, with a distal end of the connector conduit being adjacent to the cutting element during a procedure for implanting the connector conduit within the organ wall. The retractor element preferably includes a retractor body movably disposed within said hole forming element and an expansion element disposed on a distal end of said retractor body, the expansion element being expandable.

Figure 2A:
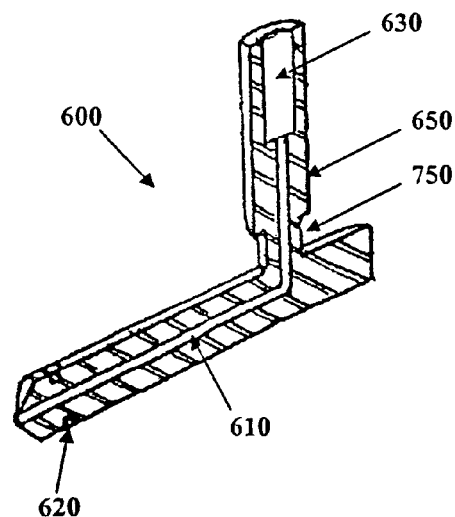
FIGS. 2A-2C illustrate are cross-sectional views of a sequencing bolt, retractor body, expanding element, positioning means, and cutting element described in U.S. Patent Application Publication No. 2005-0251187.
Figure 2B:
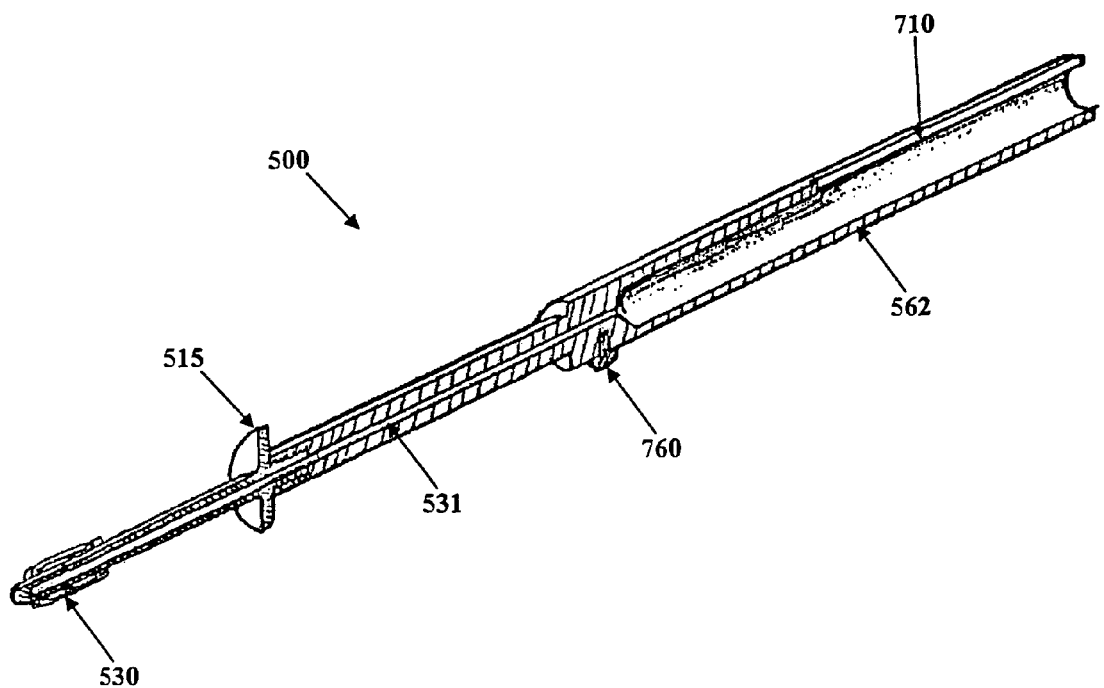
Figure 2C:
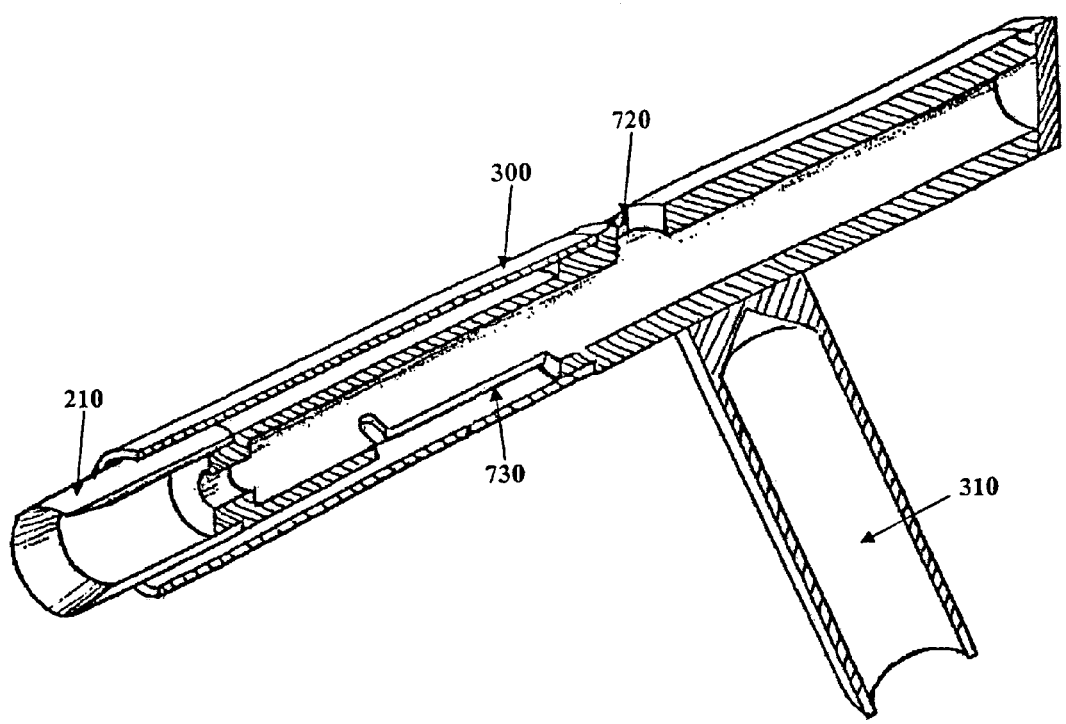

FIGS. 2A-2C illustrate components of a preferred embodiment of U.S. Patent Application Publication No. 2005-0251187, which is shown in FIGS. 4A-4E. This embodiment uses a sequencing element to coordinate the position of retractor element 500 with the expansion of expanding element 530 (FIG. 2). In this embodiment, the sequencing element is a cam mechanism. The cam mechanism helps to ensure proper use of the applicator during implantation of connector conduit 100 (See FIG. 1). As shown in FIG. 2B, retractor element 500, referred to as the retractor assembly, includes cylinder portion 562 integrated therein. The retractor assembly is positioned concentrically within pushing element 300 during use. The retractor assembly contains elements of the cam mechanism formal therein, including cylinder cam slot 710, which is a slot cut completely through the cylinder 562 wall, and a retractor cam follower 760, which may be a pin or screw in cylinder 562 (as shown) or may be an integral part of cylinder 562. Retractor element 500 may include a section of increased diameter such as stopper disk 515 to prevent cutter element 210 from cutting the heart when retractor element 500 is initially inserted. FIG. 2A illustrates plunger 600 (in the form of a sequencing bolt as described below), which is positioned concentrically within cylinder 562 during use. Plunger 600 contains elements of the cam mechanism, including bolt portion 650 with plunger cam follower 750. Plunger cam follower 750 moves within cylinder cam slot 710 and pusher cam slot 720. Plunger 600 includes passage 610 and purge/fill valve 630 (valve body not shown). Valve 630 can be opened to allow fluid flow into and out of passage 610. When closed, valve 630 allows no fluid flow in either direction. Valve 630 may be connected (such as with a catheter) to a reservoir of saline, for example, to purge the expanding element 530, access passage 531 and any other volume in the flow circuit of air before filling these volumes with fluid (such as saline). O-ring groove 620 of plunger 600 contains an o-ring (not shown) to prevent loss of fluid.

FIG. 2C illustrates a positioning assembly, which is made up of rigidly connected components including pushing element 300, cutting element 210, and handle 310. The pusher element contains elements of the cam mechanism, including pusher cam slot 720 and retractor cam slot 730. The pusher cam slot 720 is a slot cut completely through the pushing element 300 wall to accommodate plunger cam follower 750.

In addition, the '187 patent application publication discloses that the expansion element may be expandable from an unexpanded state to fully expanded state and to a partially expanded state. In this case, the sequencing means may also include a means for causing the elements to assume the following states in seriatim. The first state is a state in which the sequencing bolt is moved in the first slot and the cam slot to expand the expansion element while the retractor element is locked in a fully extended position relative to the hole forming element. The second state is a state in which the sequencing bolt is moved in the first slot and the cam slot to retain the expansion element as fully expanded. The third state is a state in which the sequencing bolt moves in the first slot and the retractor follower moves in the second slot to release the retractor element and permit the spring to move the retractor element toward the hole forming element. The fourth state is a state in which the sequencing bolt moves in the first slot while being locked in the cam slot and the retractor follower moves in the second slot to complete forming of the hole and allow insertion of the connector conduit into the hole. The fifth state is a state in which the sequencing bolt moves in the first slot and in the cam slot to release the sequencing bolt from a locked position in the cam slot to allow the expansion element to assume the partially expanded state while the expansion element is moved to be at least partially disposed in the hole forming element.

Figure 3A:
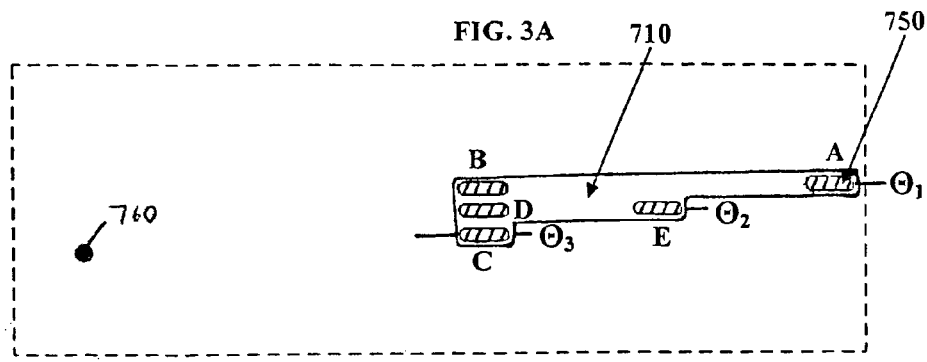
FIGS. 3A-3C illustrate the sequencing can mechanism disclosed in U.S. Patent Application Publication No. 2005-0251187 in various states.
Figure 3B:
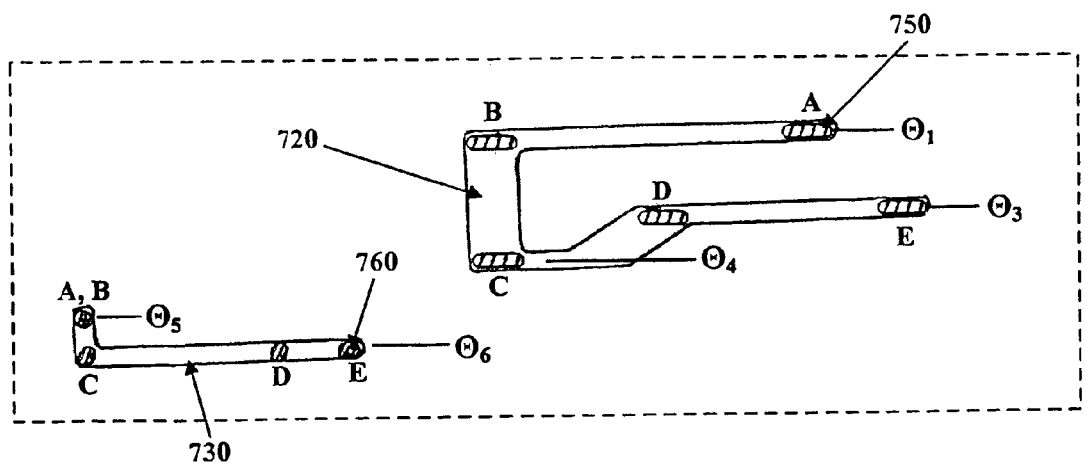
Figure 3C:
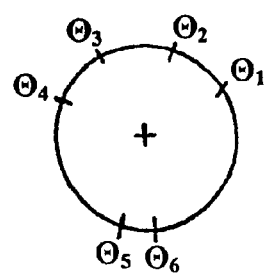
Figure 4A:
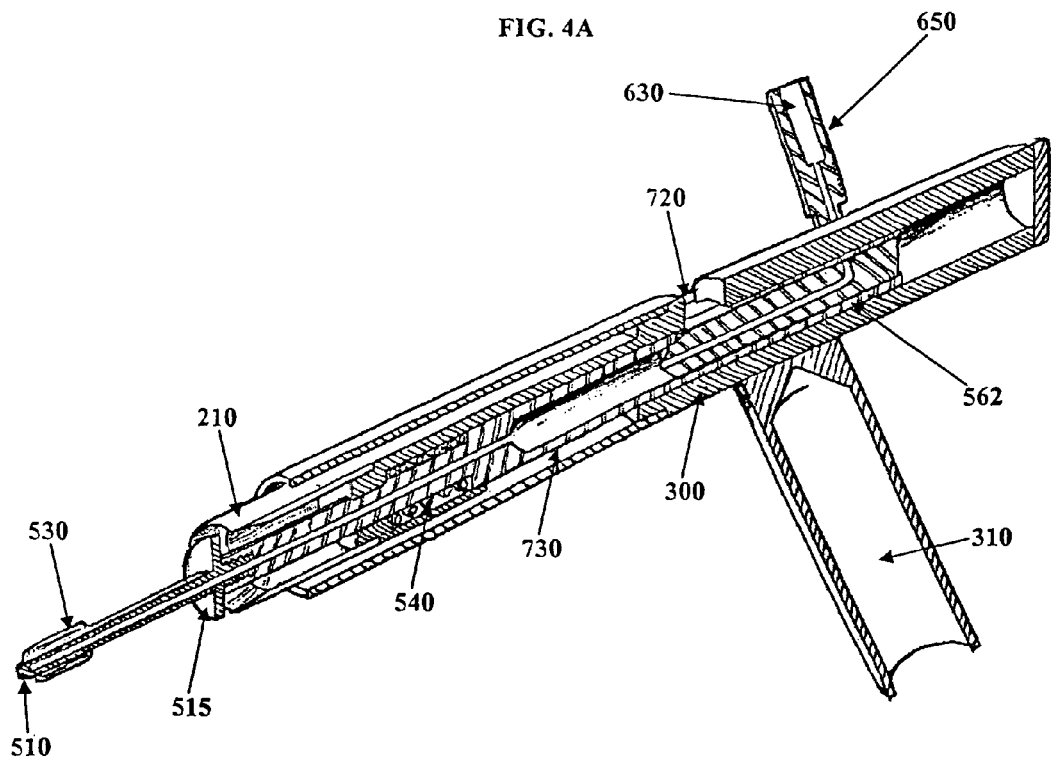
FIGS. 4A-4E illustrate a cross-sectional view of the applicator disclosed in U.S. Patent Application Publication No. 2005-0251187 in various states.
Figure 4B:
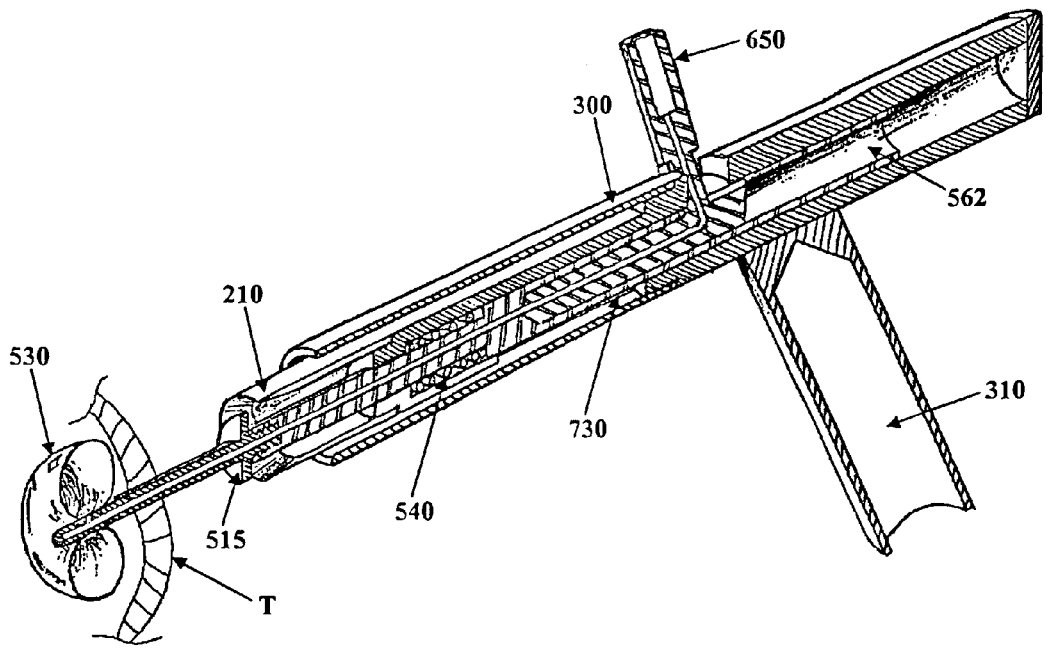
Figure 4C:
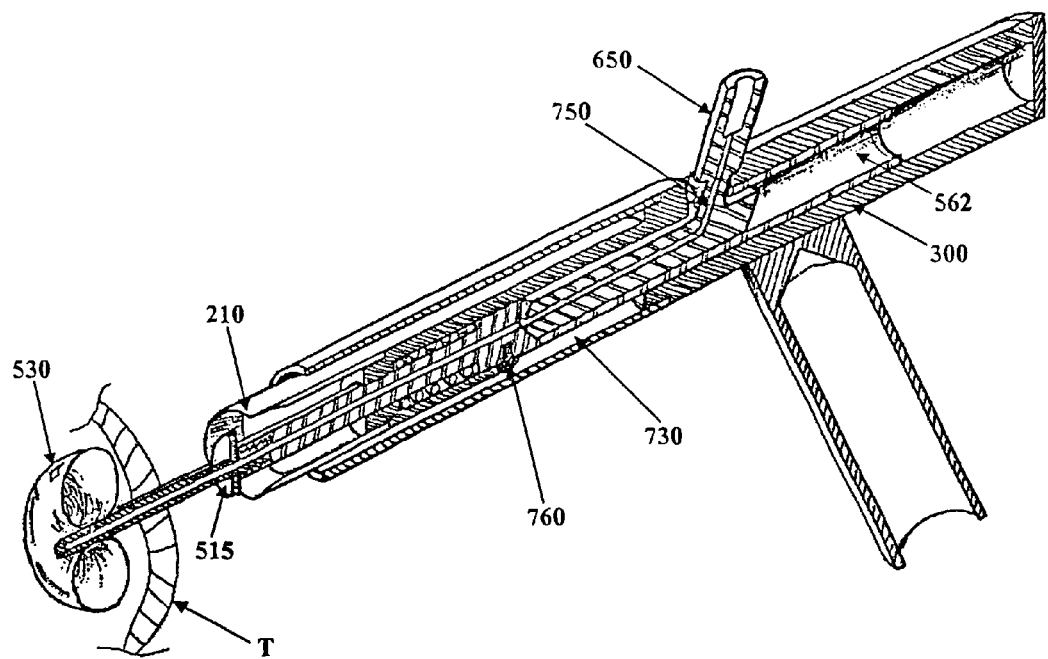
Figure 4D:
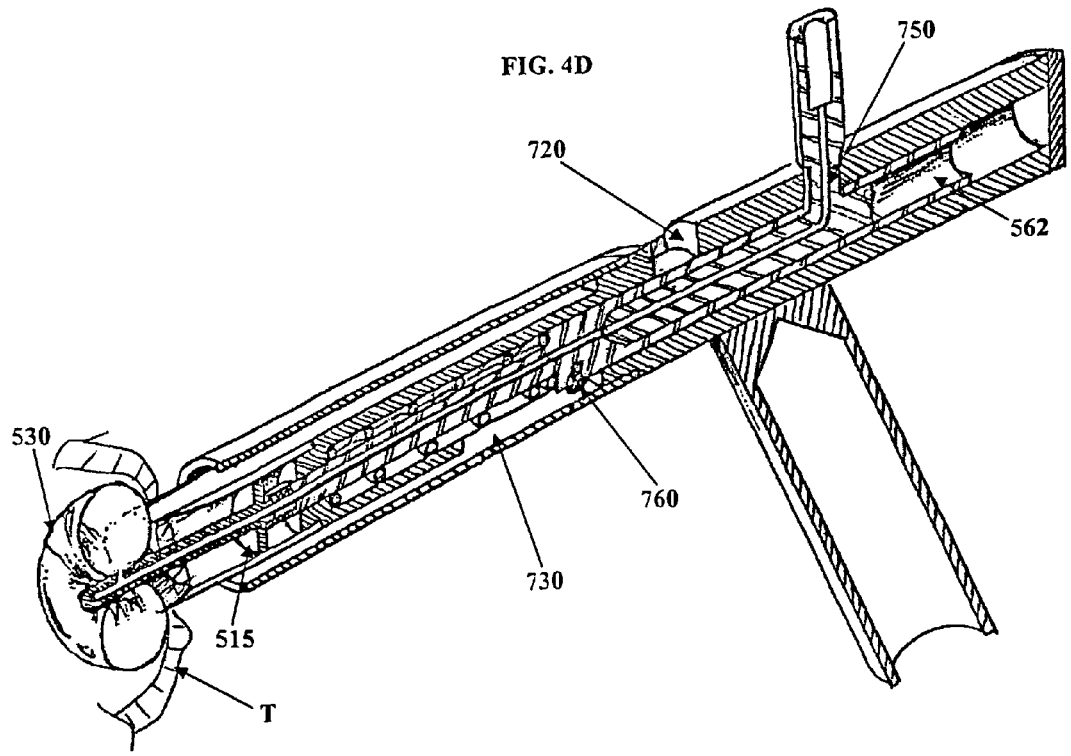
Figure 4E:
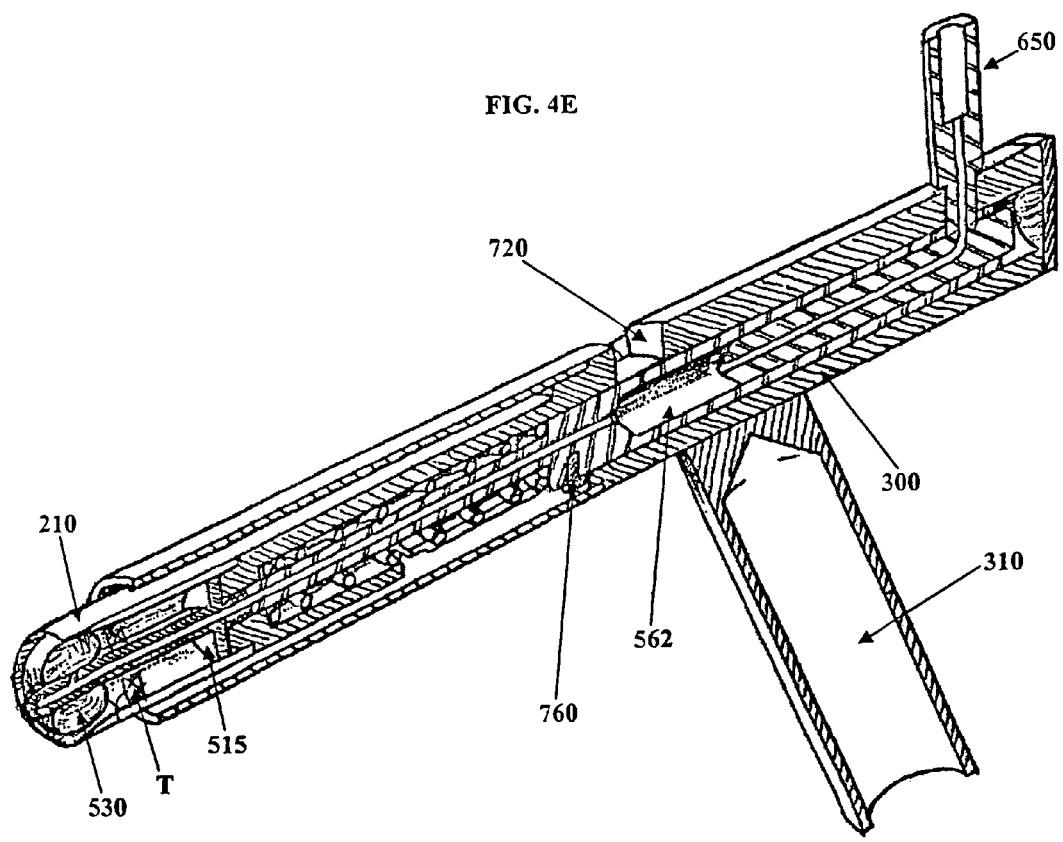

FIGS. 3A-3C illustrate operation of the cam mechanism disclosed in U.S. Patent Application Publication No. 2005-0251187. FIG. 3A illustrates cylinder cam slot 710 cut into cylinder 562 of FIG. 2B. Cylinder cam slot 710 contains three interconnected axial cam slots at angles $\theta_1$, $\theta_2$, and $\theta_3$ around the circumference of cylinder 562, as further illustrated in FIG. 3C. The axial cam slot at each angle corresponds to a range of allowable axial positions of plunger 600 within cylinder 562. At angle $\theta_1$, the axial length of the cam slot corresponds to the maximum stroke of plunger 600 within cylinder 562. This maximum stroke allows filling the expanding element 530 from minimum volume to maximum volume. At angle $\theta_2$, the axial cam slot allows plunger 600 movement to provide expanding element 530 volumes ranging from maximum volume to an intermediate volume (at an intermediate stroke) that is greater than minimum volume but less than maximum volume. At angle $\theta_3$, the axial cam slot retains plunger 600 at the position of maximum volume of the expanding element 530. FIG. 3A also illustrates positions A, B, C, D and E of plunger cam follower 750 within cylinder cam slot 710 during the steps of operation.

FIG. 3B illustrates pusher cam slot 720 and retractor cam slot 730 cut into the pusher element of FIG. 2C. FIG. 3B also illustrates positions A, B, C, D and E of plunger cam follower 750 within pusher cam slot 720 and retractor cam follower 760 within retractor cam slot 730 during the steps of operation. FIG. 3C illustrates angles $\theta_1$ to $\theta_6$ for cylinder 562 and the pusher element. For purposes of description, the value of the angles increases from $\theta_1$ to $\theta_6$. Pusher cam slot 720 includes angles $\theta_1$ and $\theta_3$, which may correspond with angles $\theta_1$ and $\theta_3$ of cylinder 562 (see FIG. 3A). Pusher cam slot 720 includes angle $\theta_4$, which is larger than $\theta_3$. The axial length of pusher cam slot 720 from position A to position B corresponds to the maximum stroke of the plunger 600, as described above. The axial length of pusher cam slot 720 from position C to position E corresponds to the intermediate stroke plus the axial distance traversed by retractor cam follower 760 from position C to position E in retractor cam slot 730. Retractor cam slot 730 includes angles $\theta_5$ and $\theta_6$. Positions A and B at angle $\theta_5$ prevent compression spring 540 from displacing cylinder 562 within the pusher element.

In operation, retractor cam slot 730 controls the motion of cylinder 562 within the pusher element. As shown in FIG. 3A and FIG. 3B, when plunger cam follower 750 (of sequencing bolt 600) is moved circumferentially from position B to position C in both cylinder cam slot 710 and pusher cam slot 720, retractor cam follower 760 is forced from position B to position C in retractor cam slot 730, which allows compression spring 540 (see FIG. 18) to push cylinder 562 axially within the pusher element. Retractor cam follower 760 within retractor cam slot 730 holds cylinder 562 at a constant angular position relative to the pusher element during movement from position C to positions D and E; therefore, movement of plunger cam follower 750 from position C to position D within pusher cam slot 720 forces cam follower 750 into the axial slot corresponding to angle $\theta_2$ of cylinder 562.

Referring to FIGS. 4A-4E, the applicator of U.S. Patent Application Publication No. 2005-0251187 is shown at various steps during use. FIG. 4A to FIG. 4E correspond to positions A to E, respectively, which are described in FIG. 3A to FIG. 3C. Recognizing that individual surgeons may find alternative steps to properly use the invention, a representative sequence of steps for use of the applicator to implant a connector conduit is described. Sequencing bolt 600 is moved from position A to position B to inflate the balloon behind tissue T of the heart wall (see FIG. 4B). The surgeon moves sequencing bolt 600 from position B to position C (see FIG. 4C) and then releases sequencing bolt 650. Beginning at position C of FIG. 4C, compression spring 540 pushes the retractor assembly from, position C to position D (see FIG. 4D). When the retractor assembly moves from position C to position D, tissue T of the heart wall is first sandwiched between the balloon and the sharpened edge of the cutting element 210a. By the surgeon using handle 310 to apply axial force and back-and-forth rotary motion, the sharpened edge of the cutting element 210a cuts though the heart wall to form a plug of tissue T that resides in the cutting element 210. At position D, the retractor assembly has been retracted until the balloon is in contact with cutting element 210 and the tissue plug is fully within cutting element 210. Also at position D, cylinder cam slot 710 has forced plunger cam follower 750 circumferentially to angle $\theta_2$, thereby allowing deflation of the balloon to begin. Between position D (FIG. 4D) and position E (FIG. 4E), the balloon deflates to the intermediate volume (described earlier), and the retractor assembly retracts to its final position. If necessary, the surgeon may pull sequencing bolt 600 to its final position E.

To prevent possible injury to the inner surfaces of the heart (e.g., ventricle wall, chordae tendinae), the expansion element should remain in the fully expanded state (i.e. at position D, or the fourth state, in FIG. 3B) until the connector conduit has been fully inserted and placed into its final position within the apex wall. If the connector conduit is only partially inserted at the fourth state and the expansion element is allowed to assume the partially expanded state before the connector conduit is completely inserted to its final position, the sharp edge of the hole forming element may be exposed to the inner surfaces of the heart (e.g., endocardium, chordae tendinae) during twisting and pushing motion to place the connector conduit to its final position within the apex wall, which can result in damage to the inner surfaces of the heart. In this way, the fully expanded expansion element covers the sharp edge of the hole forming element while the connector conduit is being maneuvered to its final position, thereby preventing damage to the inner surfaces of the heart.

Accordingly, the invention reduces the likelihood of damage to the inner surfaces of the heart by improving on the applicator described above by providing a safety latch that prevents proceeding from the fourth state to the fifth state described above until the safety latch is released by a deliberate action of the surgeon. In this way, the surgeon can place the connector conduit into its final position within the apex before deliberately releasing the safety latch to allow the expansion element to assume the partially expanded state.

Figure 5:
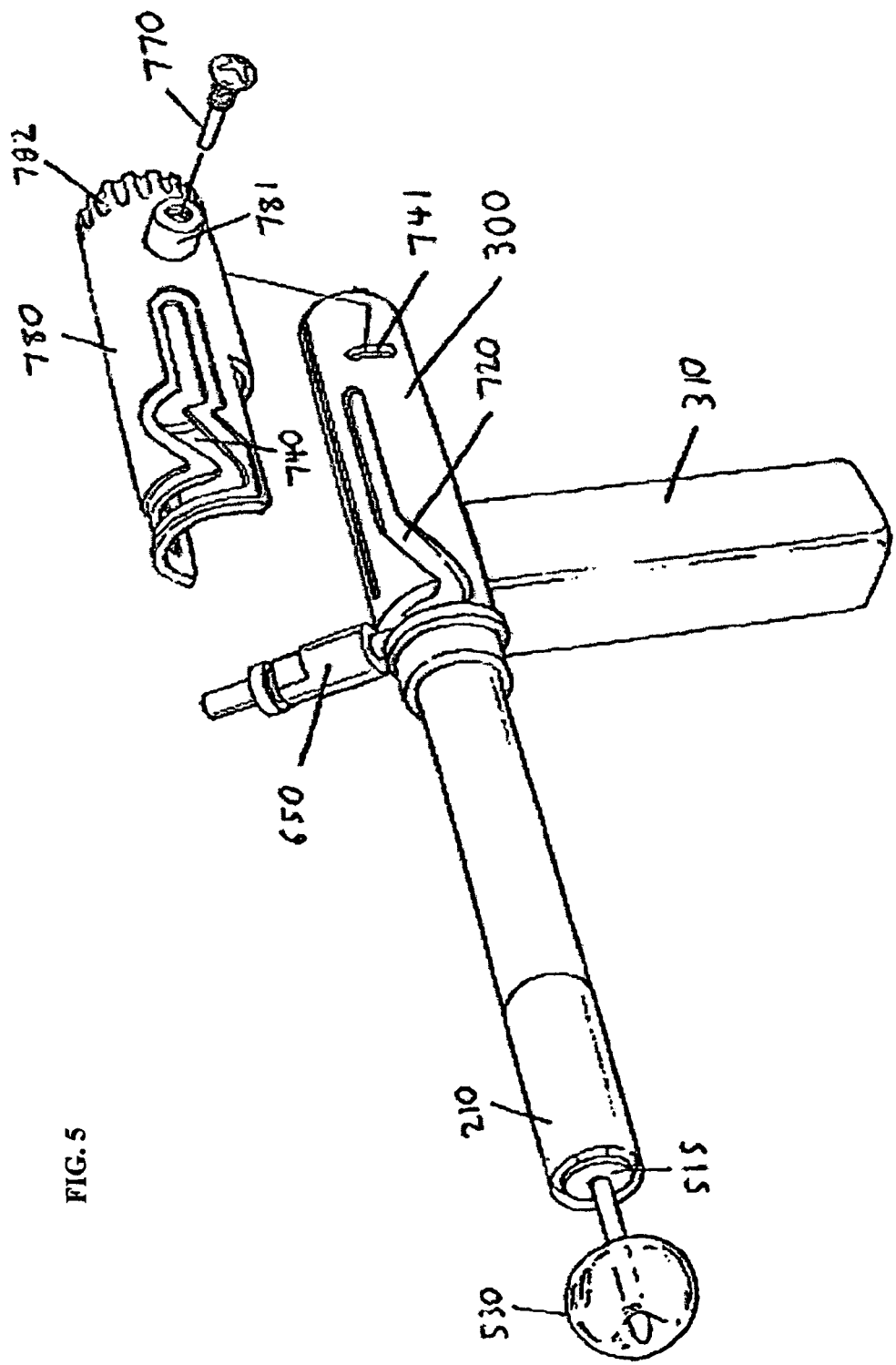
FIG. 5 is an exploded view of the applicator and safety latch of the invention.

FIG. 5 illustrates an exploded view of an exemplary applicator and safety latch of the invention. The basic components shown in FIG. 5, and their reference numerals, are identical to those disclosed in U.S. Patent Application Publication No. 2005-0251187. For example, the applicator shown in FIG. 5 includes a handle 310, an expanding element 530, a stopper disk 515, a cutter element 210, a bolt portion 650 (i.e. a sequencing bolt), and a pusher element 300. Pusher element 300 also includes a pusher cam slot 720 and a pusher latch cam slot 741. FIG. 5 further includes the safety latch element of the invention. The safety latch element of the invention includes a latch cylinder 780, which includes a safety latch cam slot 740, a lever 781, a grooved surface 782, and a spring element (not shown).

During operation, latch cylinder 780 fits concentrically over pushing element 300 such that safety latch cam slot 740 is positioned generally over pusher cam slot 720. In this configuration, sequencing bolt 650 may extend through both pusher cam slot 720 and safety latch cam slot 740. In addition, a spring element (not shown) is positioned within latch cylinder 780 such that when latch cylinder 780 is installed over pushing element 300, the spring element rotationally biases latch cylinder 780 relative to pushing element 300.

The safety latch element further includes a safety latch cam follower 770, which is, for example, a threaded pin that fits snugly in a lever 781 and extends through latch cylinder 780 into pusher latch cam slot 741. Thus, when latch cylinder 780 is rotated relative to pusher element 300, the tip of safety latch cam follower 770 moves within pusher latch cam slot 741 (shown). In addition, there is a further optional cam slot (i.e. retractor latch cam slot 742) which may be positioned in the retractor element (see FIG. 6A), which is concentrically located within pusher element 300. According to the preferred embodiment, the tip of safety latch cam follower 770 further extends through pusher latch cam slot 741 into retractor latch cam slot 742, to thereby restrict rotational movement of latch cylinder 780 with respect to both pusher element 300 and the retractor element, and vice versa. Thus, safety latch cam follow 770 with pusher latch cam slot 741 and retractor latch cam slot 742 constrain movement of latch cylinder 780 relative to pushing element 300 and the retractor element to allow only limited rotary motion. This rotary motion is facilitated with lever 781 and grooved surface 782.

FIGS. 3 and 4 illustrate the orientations and relative positioning of the slots in the retractor assembly (FIG. 3A) and the pusher element (FIG. 3B) as disclosed in the '187 patent application publication. The slots are illustrated such that, during operation, the slots in FIG. 3B would be overlaid above the slots in FIG. 3A. These figures further describe the relative movement of the retractor element and the pusher element when sequencing bolt 650 is moved through cylinder cam slot 710 of the retractor assembly and, simultaneously, pusher cam slot 720 of the pusher assembly. When plunger cam follower 750 (of sequencing bolt 650) is moved to position C in pusher cam slot 720, a compression spring 540 pushes cylinder 562 axially within the pusher element from position C to position E. (See FIG. 4).

In addition, with respect to FIGS. 3 and 4, after the sequencing bolt completes the move from position C to position E, the user may wish to reload the device by reversing the movement of the cam mechanism from position E to position C. During movement from position E to position C, the force applied to sequencing bolt 650 serves to fully inflate expanding element 530 and to compress compression spring 540. When position D is reached during reloading, if the force applied to sequencing bolt 650 to inflate expanding element 530 exceeds the force required to compress spring 540, cylinder 562 can move relative to pushing element 300, thereby misaligning the cam slots and resulting in undesired binding of the sequencing bolt 650 in the cam slots. This binding can be avoided by reducing movement of the retractor element 500 by reducing the length of the retractor cam slot 730 to stop at position D. (See FIG. 3B). As a result, expansion element 530 does not fully retract into cutting element 210. FIG. 6B illustrates an exemplary retractor cam slot 730 that has been shortened as is described above. As is clear in FIG. 6B, positions D, E, and F in retractor cam slot 730 are all in the same position.

Referring back to FIGS. 3 and 4, as plunger cam follower 750 passes position D, the hole is formed in the organ and the expansion state of the expansion element changes from a fully expanded state to a partially expanded state. When this occurs, it is possible for the expansion element to assume the partially expanded state prior to completely cutting through the wall of the organ. In addition, while the surgeon is twisting and pushing the applicator to form the hole and position the connector conduit, if used, the premature deflation of the expansion element to the partially expanded state can result in exposure of the sharp cutting edge of the hole forming element to the inner surfaces of the hollow organ (e.g., endocardium, chordae tendinae). This exposure can result in damage to the inner surfaces of the organ, possibly resulting in injury or death to the patient.

In contrast, the present invention provides a safety latch element that prevents exposure of the sharp cutting edge to the inner surfaces of the hollow organ. In particular, as is shown in FIGS. 6A-6D, which shows the planar orientations and relative positioning of the slots of the invention in the retractor assembly (FIG. 6A), the pusher element (FIG. 6B), and the safety latch (FIG. 6C), the invention includes a safety latch feature in a safety latch cam slot that stops the movement of sequencing bolt 650 at position D, and prevents proceeding from position D until the safety latch is released by a deliberate action of the surgeon. This feature is embodied in the safety latch cam slot at position D, which is located, in FIG.

6C, in a corner portion of safety cam slot 740. As mentioned above, the safety latch element also includes an internal spring element which rotationally biases the safety latch relative to the pusher assembly. In this arrangement, the spring rotationally biases the safety latch assembly in a downward direction in FIG. 6C, thereby biasing the sequencing bolt into position D of the safety latch cam slot and preventing inadvertent rotation of the safety latch cam slot relative to the pusher assembly into position E.

Figure 6A:
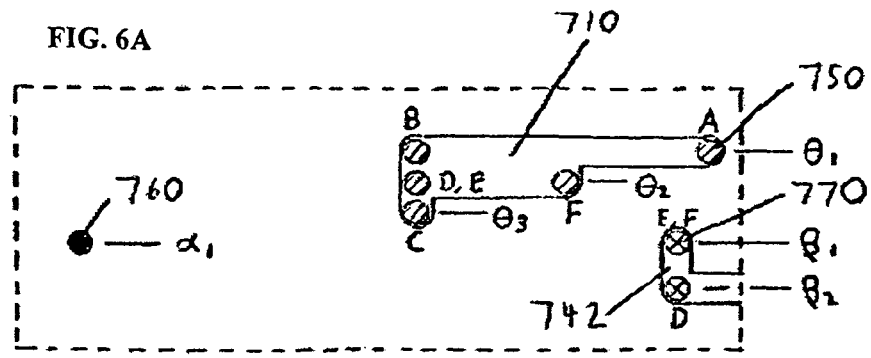
FIGS. 6A-6D illustrate the sequencing cam mechanism of the invention with a safety latch in various states.
Figure 6B:
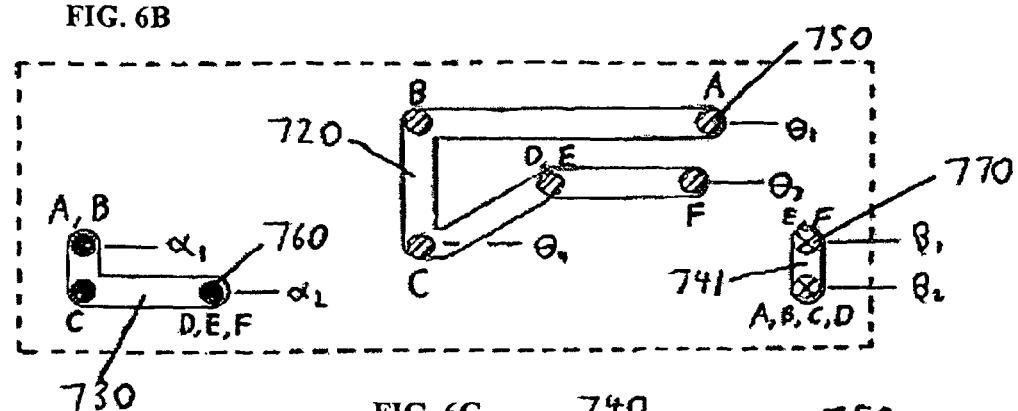

FIG. 6A is a planar representation of cylinder 562 (i.e. the retractor assembly), and illustrates the positioning of cylinder cam slot 710 and retractor latch cam slot 742 on cylinder 562. In addition, FIG. 6A illustrates the positioning of retractor cam follower 760, which is rigidly attached to cylinder 562. During operation, safety latch cam follower 770, which is inserted through latch 781 (FIG. 5) and pusher latch cam slot 741 (FIG. 6B), enters optional retractor latch cam slot 742 as the expanding element 530 approaches the sharp edge of the cutting element 210. Latch cylinder 780 can then be rotated to move safety latch cam follower 770 from position D to position E in retractor latch cam slot 742 to operationally lock cylinder 562 and the retractor assembly axially relative to the pushing element 300. This axial locking reduces movement of cylinder 562 within the pushing element 300 when sequencing bolt 650 is moved from position F to position C, such as when reloading the applicator for reuse. It should be noted that optional retractor latch cam slot 742 can be used in conjunction with, or as an alternative to, a shortened retractor cam slot 730 as a means to prevent undesired binding of the sequencing bolt in the cam slots.

Similarly, FIG. 6B is a planar representation of pushing element 300. Pushing element 300 preferably includes three slots: a retractor cam slot 730, a pusher cam slot 720, and a pusher latch cam slot 741. It should be noted that retractor cam slot 730 as described with reference to the present invention, is of a length suitable to bring the expansion element into contact with the tip of the cutting element, but is preferably not of sufficient length to cause the expansion element to withdraw into the hole forming element prior to extraction of the applicator. As is noted above, safety latch cam follower 770 is positioned within pusher latch cam slot 741. Thus, safety latch cam follower 770 is capable of movement within the limits of pusher latch cam slot 741. As can be seen in FIG. 6B, safety latch cam follower 770 can rotate within the limits of pusher latch cam slot 741. In addition, the relative positioning of the pusher assembly relative to the retractor assembly is controlled by the interactions between retractor cam follower 760 and the retractor cam slot 730. Pusher cam slot 720 is the primary slot in pushing element 300 for controlling movement of components within the applicator, such as the expansion element. Plunger cam follower 750 (of sequencing bolt 650), which also passes through safety latch cam slot 740 and cylinder cam slot 710, is positioned within pusher cam slot 720.

Figure 6C:
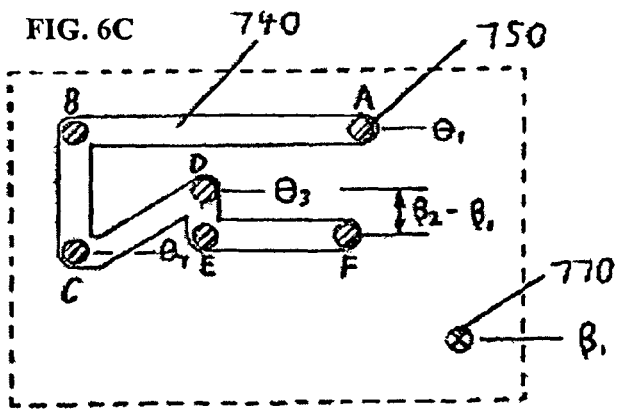

FIG. 6C is a planar representation of the safety latch element of the invention, including latch cylinder 780. Latch cylinder 780 includes a safety latch cam slot 740, through which plunger cam follower 750 passes, and latch 781, through which safety latch cam follower 770 passes. Safety latch cam follower 770 is preferably rigidly attached to latch cylinder 780. In addition, it should be noted that portions of safety latch cam slot 740 may not be fully enclosed, provided such open portions do not interfere with the functionality of the safety latch element and the movement of the sequencing bolt.

Figure 6D:
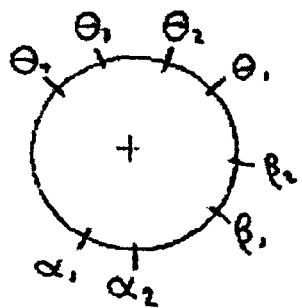

FIG. 6D illustrates angles of rotation $\theta_1$ to $\theta_4$, $\alpha_1$ to $\alpha_2$, and $\beta_1$ to $\beta_2$ for cylinder 562, pushing element 300 and latch cylinder 780. In addition, positions A, B, C, D, E and F illustrate positions of plunger cam follower 750, retractor cam follower 760 and safety latch cam follower 760 within cam slots. Each of these positions represents a state point. In the design described in FIGS. 6A-6D, cylinder 562 moves axially relative to pushing element 300 only when sequencing bolt 650 moves from position C to position D. The extent of relative movement is defined by the length of retractor cam slot 730 between position C and position D. Cylinder 562 does not move axially while expanding element 530 assumes the partial expansion state when sequencing bolt 650 moves from position E to position F.

Figure 7A:
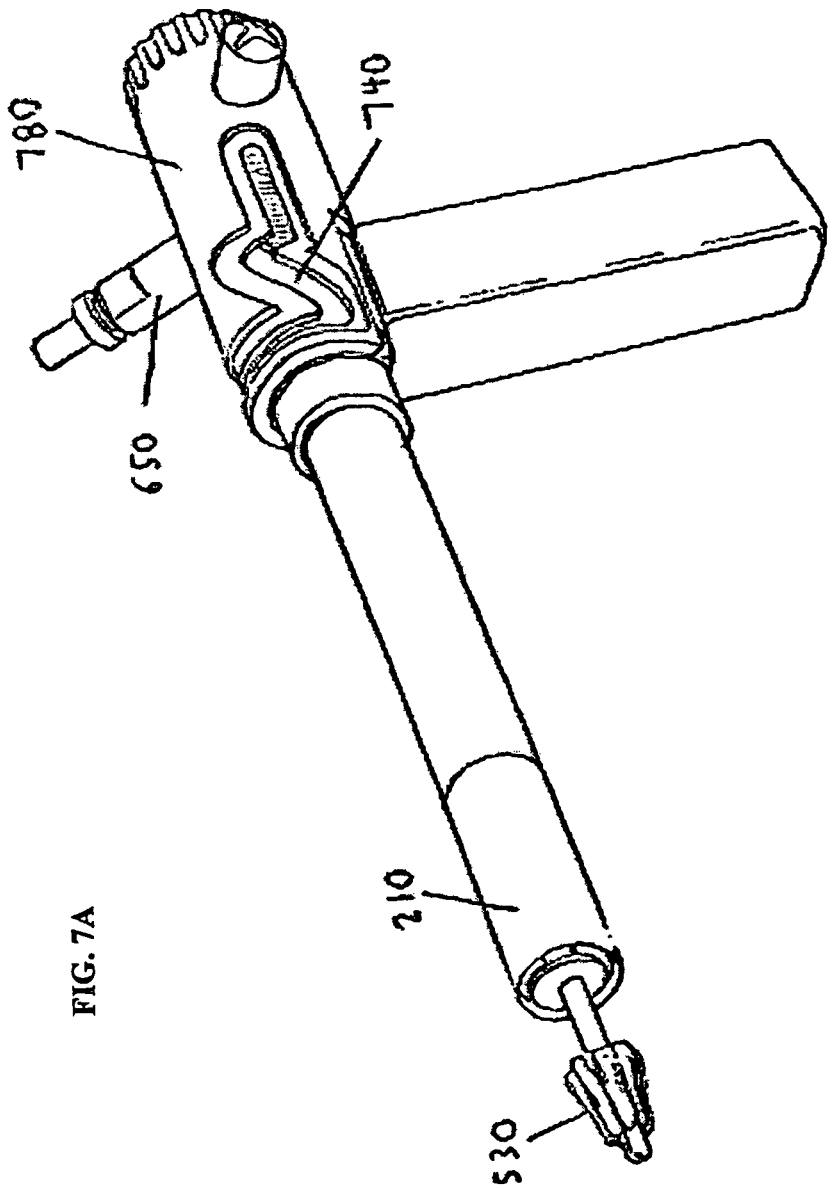
FIGS. 7A-7D illustrate the applicator of the invention with a safety latch in various states.
Figure 7B:
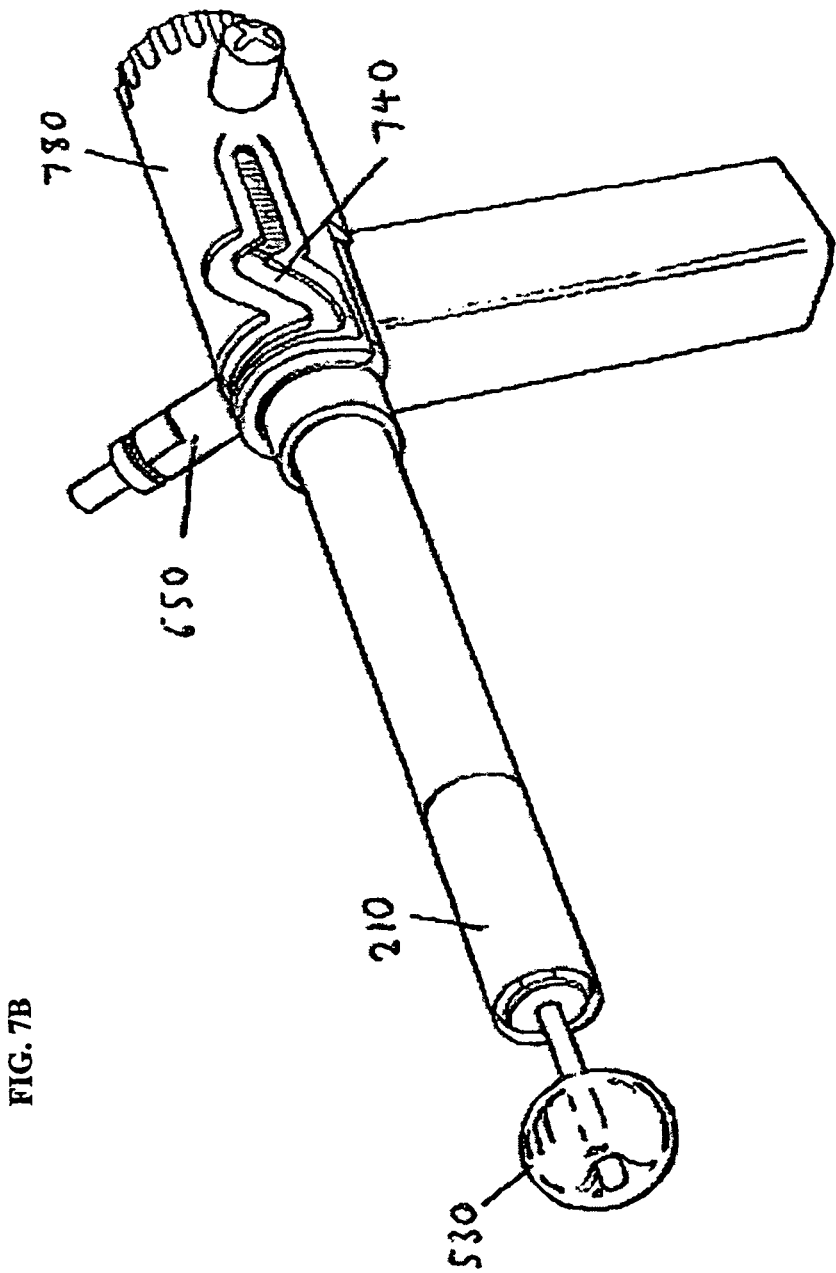
Figure 7C:
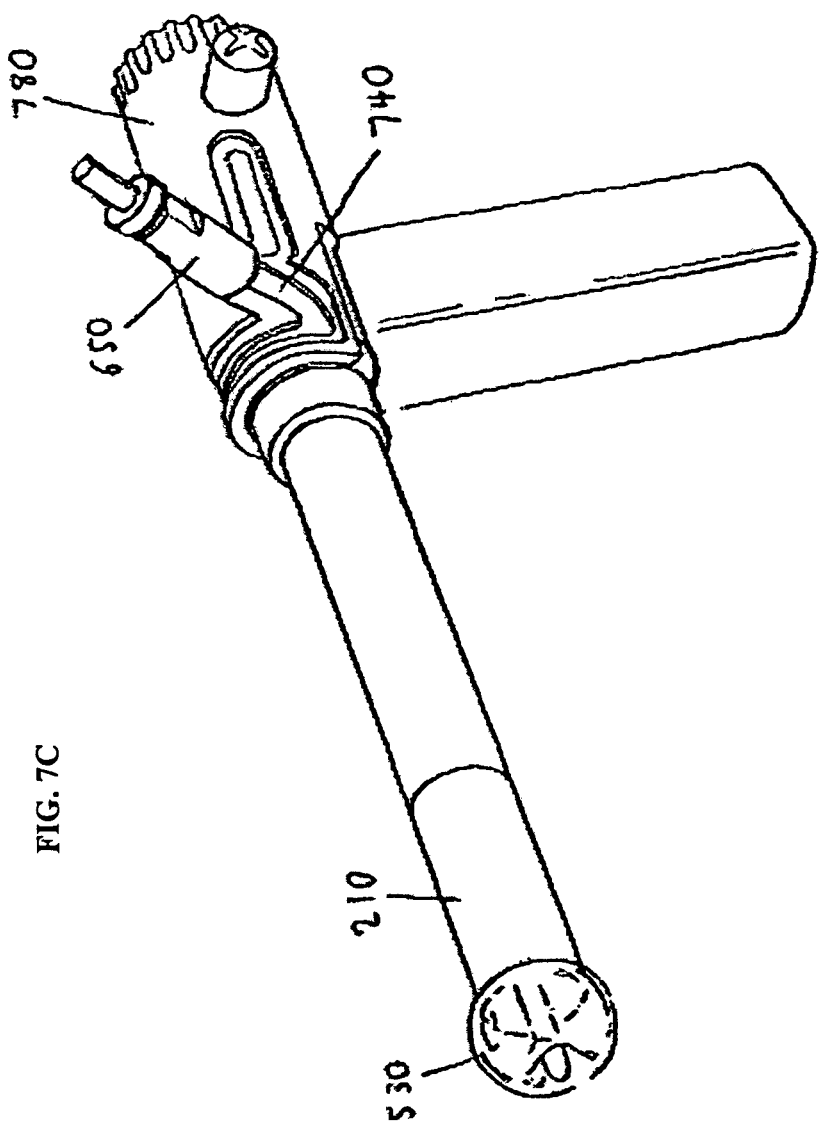
Figure 7D:
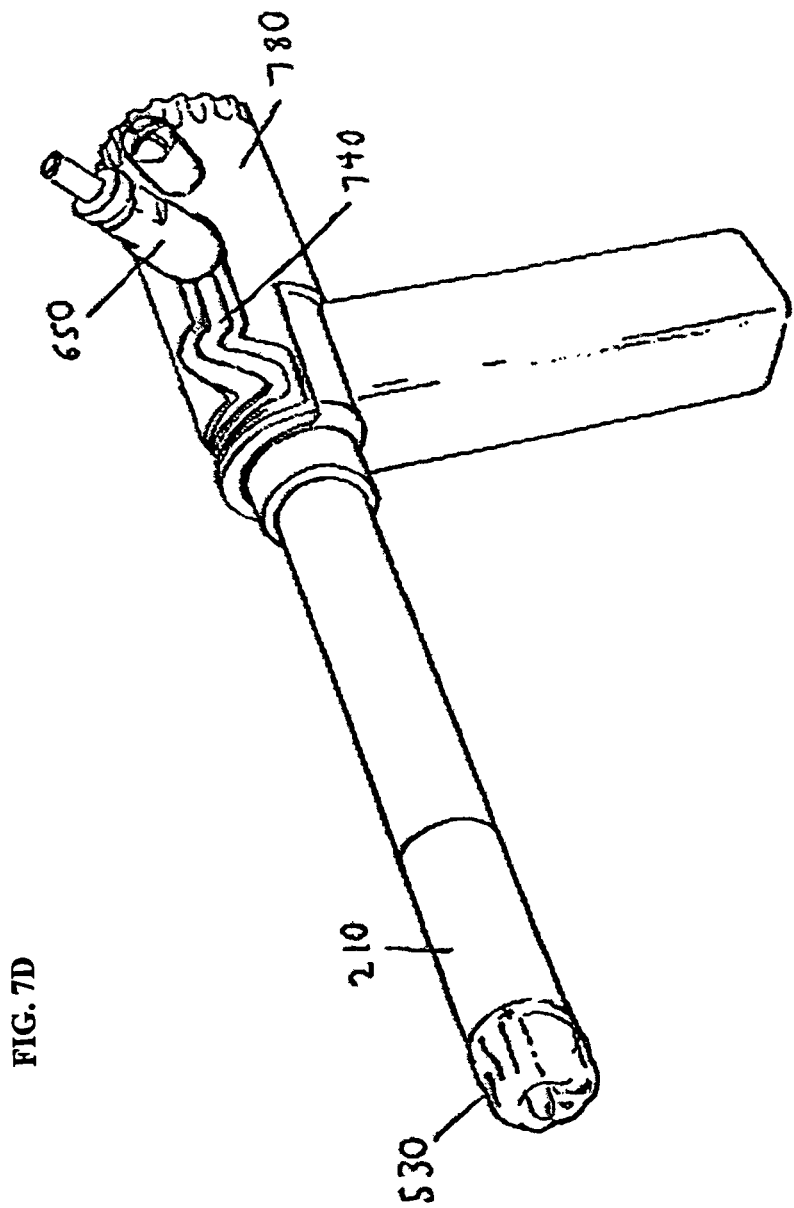

FIGS. 7A-7D represent the applicator at several state points. FIG. 7A corresponds to position. A, as described in FIG. 6A-6D. FIG. 7B corresponds to position B, as described in FIG. 6A-6D. FIG. 7C corresponds to position D, as described in FIG. 6A-6D. FIG. 7D corresponds to position F, as described in FIG. 6A-6D.

Thus, during operation, the sequencing means causes the elements to assume a plurality of distinct states. After the initial setup, each element will be in position A, with the expansion element being in a deflated state, and the retractor element being in a fully extended position. (See FIG. 7A). In this initial position, the trocar of the retractor element has already been pushed through the wall of the organ to be cut, and the deflated expansion element is positioned within the organ.

When the surgeon is ready to begin the sequencing procedure, sequencing bolt 650 is moved from position A (FIG. 7A) to position B (FIG. 7B). This movement causes plunger cam follower 750 (of sequencing bolt 650) to move from a first position (A) to a second position (B) in each of the cylinder cam slot, the pusher cam slot, and the safety latch cam slot. This movement causes the expansion element to expand to a fully expanded state while retaining the retractor element in a fully extended position relative to the hole forming element. Thus, at this point, the expansion element is in a fully expanded state within the organ. (See FIG. 7B).

Sequencing bolt 650 is then rotated from position B to position C in the cylinder cam slot, the pusher cam slot, and the safety latch cam slot, thereby retaining the expansion element in the fully expanded state and the retractor element in the fully extended position. This is a rotational step which places retractor cam follower 760 in position C in retractor cam slot 730 while retaining safety latch cam follower 770 in position C in pusher latch cam slot 741.

When sequencing bolt 650 reaches position C, compression spring 540 biases the retractor assembly, and expansion element 530, towards position D. This movement affects many of the components. For example, as sequencing bolt 650 moves from position C to position D, expansion element 530 is biased towards cutter element 210, thereby causing cutter element 210 to come into contact with the wall of the organ. The surgeon then pushes and rotates cutter element 210 to cause cutter element 210 to cut into and through the wall of the organ, thereby creating the tissue plug. When sequencing bolt 650 reaches position D, cutting element 210 comes into contact with fully expanded expansion element 530, thereby completing the cutting process of the wall of the organ. In addition, as sequencing bolt 650 moves from position C to position D, retractor cam follower 760 moves from position C to position D in retractor cam slot 730 and safety latch cam follower 770 is retained in position D in retractor latch cam slot 742. Thus, the net effect of the movement from position C to position D is to move the retractor element towards the hole forming element, thereby forming the hole with cutting element 210, while retaining the expansion element in the fully expanded state throughout the process. FIG. 7C illustrates the state of the applicator when sequencing bolt 650 is in position D.

The fourth state is a state in which sequencing bolt 650 is locked in position D. This state is made possible through the use of the safety latch of the invention. As is shown in FIG. 7C, sequencing bolt 650 is positioned in an angled portion of safety latch cam slot 740 at position D, and is in axial abutment with a side of safety latch cam slot 740, thereby preventing further axial movement of sequencing bolt 650 relative to the safety latch. Thus, in this position, the expansion element is retained in the fully expanded state. In addition, at position D, expanding element 530 is in contact with the sharp edge of cutting element 210. At position D, the expanding element 530 has sufficient stiffness and is of sufficiently larger diameter than cutting element 210 to prevent the sharp edge of cutting element 210 from contacting the inside surface of the organ, which, in the case of a heart, is the ventricle. Protecting the inner surface of the organ from the sharp edge allows the surgeon to twist and push the connector conduit to its final position, if a connector conduit is used.

When the user is ready to extract the applicator from the organ (i.e. when the connector conduit, if used, is installed in its final position), the user may use lever 781 or grooved surface 782 to deliberately rotate the safety latch element relative to sequencing bolt 650. This movement repositions sequencing bolt 650 from position D to position E in safety latch cam slot 740. The position of sequencing bolt 650 does not change relative to pusher cam slot 720 or cylinder cam slot 710 during this repositioning.

As soon as the safety latch element is rotated relative to sequencing bolt 650, thereby causing sequencing bolt 650 to be repositioned in position E in safety latch cam slot 740, the sequencing bolt exits the axial abutment it had with the side of safety latch cam slot 740, and the pressure from the compression of expansion element 530 axially biases sequencing bolt 650 towards position F. As sequencing bolt 650 approaches position F, expansion element 530 collapses from a fully expanded state to a partially expanded state. As is shown in FIG. 7D, when sequencing bolt 650 reaches position F, partially expanded expansion element 530 is pressed against cutting element 210, which is ideal for extraction of the applicator from the organ and connector conduit, if used.

The design of the safety latch ensures that rotation of latch cylinder 780 relative to pushing element 300 results in partial deflation of the expanding element 530 only when the sequencing bolt 650 is at position D before rotation. This design provides a safety latch that the surgeon cannot deliberately or inadvertently release before the sequencing bolt 650 is at position D.

Thus, through the use of the safety latch element, the expansion element remains in its fully expanded state at position D, and is prevented from changing from the fully expanded state to the partially expanded state until the surgeon deliberately chooses to do so. By retaining the expansion element in the fully expanded state, the safety latch enables the sharp edge of the hole forming element to be completely covered by the fully expanded expansion element, thereby preventing exposure of the inner surfaces of the organ to the sharp edge of the hole forming element, and the possibility of resulting damage to the inner surfaces of the organ.

Furthermore, in some circumstances, surgeons may wish to cut a hole in the wall of a hollow organ, such as the heart, without simultaneously inserting a connector conduit into the hole. Accordingly, the present invention may be used solely to cut a hole in the heart wall, and does not require simultaneous insertion of a conduit connector or other device. The connector conduit could be implanted in the hole as a separate step.

What is claimed is:

1. An applicator for forming a hole in a wall of a hollow organ comprising:
   a hole forming element for forming a hole in the wall of the organ, the hole forming element having a cutting element on a distal end thereof;
   a positioning element coupled to the hole forming element for positioning the hole forming element;
   retractor element operatively coupled to the positioning element; and
   a sequencing element for coordinating the relative movement of the retractor element and the hole forming element in a sequential manner to thereby carry out a procedure for forming a hole in the wall of the hollow organ;
   wherein the retractor element comprises a retractor body movably disposed within the hole forming element and an expansion element disposed on a distal end of the retractor body, the expansion element being expandable;
   wherein the expansion element is expandable from an unexpanded state to fully expanded state and to a partially expanded state;
   wherein the sequencing element controls the expansion of the expansion element from the unexpanded state, to the fully expanded state, and to the partially expanded state in a sequential manner;
   wherein the sequencing element further comprises a safety latch element operatively coupled to the retracting element and the hole forming element; and
   wherein the sequencing element further comprises a sequencing bolt that extends through a cylinder cam slot formed in the retractor element, a pusher cam slot formed in a pusher element, and a safety latch cam slot formed in the safety latch element.

2. The applicator of claim 1, wherein the sequencing element comprises a mechanism for causing the elements to assume the following states in seriatim:
   a) a first state in which the sequencing bolt moves from a first position to a second position in each of the cylinder cam slot, the pusher cam slot, and the safety latch cam slot, thereby expanding the expansion element to a fully expanded state while retaining the retractor element in a fully extended position relative to the hole forming element;
   b) a second state in which the sequencing bolt moves from the second position to a third position in the cylinder cam slot, the pusher cam slot, and the safety latch cam slot, thereby retaining the expansion element in the fully expanded state and the retractor element in the fully extended position;
   c) a third state in which the sequencing bolt moves from the third position to a fourth position in the cylinder cam slot, the pusher cam slot, and the safety latch cam slot, thereby permitting the retractor element to move towards the hole forming element while retaining the expansion element in the fully expanded state;
   d) a fourth state in which the sequencing bolt is locked in a fourth position in the safety latch cam slot, the cylinder cam slot, and the pusher cam slot, thereby retaining the expansion element in the fully expanded state;
   e) a fifth state in which the safety latch element is moved relative to the retractor element such that the sequencing bolt is repositioned from the fourth position to a fifth position in the safety latch cam slot while remaining in the fourth position in the cylinder cam slot and the pusher cam slot, thereby releasing the expansion element from the fully expanded state; and f) a sixth state in which the sequencing bolt moves from the fifth position to a sixth position in the safety latch cam slot, and simultaneously, from the fourth position to a fifth position in the cylinder cam slot and the pusher cam slot, to allow the expansion element to assume the partially expanded state.

3. The applicator of claim 1, wherein the organ is a heart.

4. The applicator of claim 1, further comprising a connector conduit coupled to the hole forming element.

5. The applicator of claim 1, wherein the expansion element is a balloon.

6. The applicator of claim 1, wherein the expansion element is an expandable sponge.

7. The applicator of claim 1, wherein the expansion element is an umbrella mechanism.

8. The applicator of claim 1, wherein the sequencing element comprises a cam mechanism.

9. The applicator of claim 1, wherein the sequencing element comprises a gear mechanism.

10. The applicator of claim 1, wherein the sequencing element comprises at least one servo mechanism operatively coupled to the positioning element and a controller operatively coupled to the at least one servo mechanism.

11. The applicator of claim 10, further comprising a button operatively coupled to the sequencing element for activating the sequencing element upon depression of the button to thereby accomplish steps of a procedure for implanting the connector conduit within the organ wall.

\* \* \* \* \*